United States Patent [19]

Tsuda et al.

[11] 4,402,315
[45] Sep. 6, 1983

[54] INHALATION TOXICITY TESTING APPARATUS

[75] Inventors: Shuji Tsuda, Tokorozawa; Makoto Iwasaki, Toride, both of Japan

[73] Assignee: Tokiwa Kagaku Kikai Co., Ltd., Tokyo, Japan

[21] Appl. No.: 264,770

[22] Filed: May 18, 1981

[30] Foreign Application Priority Data

May 29, 1980 [JP] Japan .................................. 55-71677

[51] Int. Cl.³ ............................................ A61M 15/00
[52] U.S. Cl. ............................... 128/200.18; 128/716; 128/747; 128/203.12
[58] Field of Search ............. 128/747, 200.18, 200.14, 128/207.18, 203.12, 716

[56] References Cited

U.S. PATENT DOCUMENTS 2,826,454  3/1958  Coanda ...................... 128/200.18 X
3,236,458  2/1966  Ramis ......................... 128/200.18 X
4,116,387  9/1978  Kremer et al. ............. 128/200.18 X Primary Examiner—Kyle L. Howell
Assistant Examiner—John C. Hanley
Attorney, Agent, or Firm—Wenderoth, Lind & Ponack

[57] ABSTRACT

In an inhalation toxicity testing apparatus of the type wherein the noses or heads of test animals are exposed to the mist of a test liquid, a vertical cylindrical housing defining a chamber for the passage of the mist is provided with a plurality of circumferentially spaced-apart openings each adapted to receive the nose or head of a test animal, means for supplying the test liquid mist into the chamber is disposed in the housing below the openings, and an outlet is formed at the top of the housing whereby the mist flows upward the chamber. Means for controlling the droplet size distribution of the mist is also provided to remove relatively large size droplets from the mist.

7 Claims, 5 Drawing Figures

INHALATION TOXICITY TESTING APPARATUS

BACKGROUND OF THE INVENTION

This invention relates to an apparatus for testing the inhalation toxicity of chemical agents such as agricultural chemicals on small animals such as rats, and more particularly, to such an apparatus for exposing the noses or heads of animals to the mist of a test liquid so that the animals may inhale the mist.

In general, inhalation toxicity test are performed by exposing rats or other small test animals to the mist of an agent to be tested, that is, a dispersion of droplets of a test agent in air or another suitable gas when the test agent is liquid, or a dust or fume in which particles of a test agent are dispersed in air or another suitable gas when the test agent is solid, or air containing a gaseous test agent. The influence of the test agent inhaled on test animals is observed to evaluate the toxicity of the agent. The typical inhalation toxicity test is an acute inhalation toxicity test wherein the toxicity of a chemical agent is usually evaluated in terms of the concentration of the agent at which one-half of test animals are killed upon exposure for a predetermined time (that is, median lethal concentration $LC_{50}$).

In these inhalation toxicity tests, the chemical agent inhaled in the form of mist reaches the lung of a test animal by way of its nasal or oral cavity and air-passages (trachea and bronchial tube). Thus, the inhaled agent is deposited on the nasal or oral cavity and air-passages as well as the lung. The distribution of the agent deposited on these organs widely varies with the size of droplets or particles when the agent is in the form of mist or dust. In general, the majority of relatively large size droplets or particles deposit on the nasal or oral cavity while the minority reach the lung. The smaller the size of droplets or particles, the more they reach the lung. The minority of relatively small size droplets or particles deposit on the nasal or oral cavity while the majority reach the lung. The influence of a chemical agent on an animal varies depending on a particular organ on which the inhaled agent is predominantly deposited. Test animals which are exposed to mists of the same agent at an equal concentration in different runs are affected to a different degree or in a different way if droplets in the mists are different in size for each run. Then, when acute inhalation toxicity tests are repeated using the same agent, the results or median lethal concentration values will show a variation depending on the size of droplets and the distribution thereof. Conversely, even when median lethal concentration values are equal, these values must be compensated with respect to the droplet size and its distribution before the true toxicity of an agent can be determined. For these reasons, in order that accurate toxicity evaluation is achieved in inhalation toxicity tests, particularly those tests using mist, the mist to which test animals are exposed must have a controlled droplet size distribution, particularly a uniform droplet size distribution in which the droplet size is less than a given value. The mist is preferably free of unexpectedly large size droplets.

The inhalation toxicity test may be performed in two methods, full and local exposure methods. In the full exposure method, a rat or another small animal is fully exposed to the atmosphere of a chemical agent. In the local exposure method, only the head or nose of an animal is exposed. The latter is preferred to correctly evaluate the inhalation toxicity of an agent because the agent is percutaneously taken in by the animal in addition to the inhalation through the respirator in the former method.

One example of prior art apparatus for use in inhalation toxicity tests according to the local exposure method is illustrated in FIG. 5. This apparatus comprises a vertical, hollow cylindrical housing 1 defining an inhalation chamber therein. The side wall of the housing 1 includes a plurality of circumferentially spaced-apart openings 2 to each of which a holder 4 for holding a test animal is attached such that the head or nose of the animal is faced to the chamber. Located at the top 1A of the housing 1 is means for supplying the mist of a test agent, for example, a spray nozzle 5 for atomizing a test liquid. The heads or noses of test animals are thus exposed to the mist flowing down the chamber as shown by dot-and-dash line arrows. The use of the spray nozzle 5 is insufficient to provide the mist with a uniform droplet size distribution. There often occur variations in droplet size and such variations are inconsistent in successive runs. Further some fine droplets impinge or contact with each other to coalesce into relatively large size droplets before they are inhaled by the animals during the downward travel from the nozzle 5 to the openings 2. That is, the mist that the animals inhale usually has a widely varying droplet size distribution and tends to contain unexpectedly large size droplets. It is thus difficult to achieve accurate toxicity evaluation. The mist may be passed through a classifier to provide a uniform droplet size distribution before it is introduced into the chamber. It is still difficult to avoid the tendency that fine droplets coalesce into relatively large size droplets during the downward travel from the top to the openings or before the mist is inhaled by test animals. In addition, even after relatively large size droplets have been removed from the mist by the classifier, droplets can coalesce into large size droplets during the travel from the classifier to the inlet of the chamber. It is thus difficult to prevent unexpectedly large size droplets from being inhaled by test animals.

It is, therefore, a primary object of the present invention to provide an inhalation toxicity testing apparatus in which test animals are exposed to the mist of a test liquid with unexpectedly large size droplets removed, thereby ensuring accurate toxicity evaluation.

Another object of the present invention is to produce the mist of a test liquid which has a controlled or uniform droplet size distribution upon exposure of test animals thereto, thereby achieving more accurate toxicity evaluation.

A further object of the present invention is to produce the mist of a test liquid having a uniform concentration and a uniform droplet size distribution when an inhalation test is simultaneously performed on a plurality of test animals.

A still further object of the present invention is to reduce the amount of a test liquid consumed in vain.

SUMMARY OF THE INVENTION

According to the present invention, there is provided an inhalation toxicity testing apparatus of the type wherein the noses or heads of test animals are exposed to the mist of a test liquid, which comprises a vertical, hollow cylindrical housing defining a chamber for the passage of the mist. The side wall of the housing include a plurality of circumferentially spaced-apart openings each adapted to receive the nose or head of a test animal. The housing has an outlet at the top for exhausting the mist therethrough. Means for supplying the test liquid mist into the chamber is disposed in the housing below the openings. The test liquid mist flows upward the chamber. During the upward flow of the mist from the mist supplying means to the openings, relatively large size droplets which we initially contained in the mist or newly formed through coalescence as a result of relative contact between small size droplets settle down because of their own weight under gravity. It is thus avoided that the test animals inhale relatively large size droplets.

In a preferred embodiment, the mist supplying means includes mist generating means for atomizing the test liquid into mist, and means disposed in fluid communication with the mist generating means for controlling the droplet size distribution of the mist by removing relatively large size droplets. The control means includes a casing disposed at the bottom of the housing and defining a mist reservoir. The upper portion of the casing is conical and has a vertically extending injection port at the apex for injecting the mist from the mist reservoir into the chamber. A horizontal baffle is located within the housing below the openings, but immediately above the injection port in the casing. The baffle, which is preferably a disc, has a substantially smaller configuration than the housing to leave a free space therebetween for the passage of the mist. The mist generating means may be a spray nozzle having a spraying port located at the bottom of the casing. The spray nozzle atomizes the test liquid to produce a mist. After entering the reservoir from the spraying port, the mist is injected through the injection port to impinge against the baffle, thereby removing relatively large size droplets from the mist. As a result, the mist having a controlled uniform droplet size distribution flows upward the chamber via the free space outside the baffle while newly coalescing large size droplets settle down.

BRIEF DESCRIPTION OF THE DRAWING

The inhalation toxicity testing apparatus according to the invention is described in further detail by referring to the attached drawings, in which.

DESCRIPTION OF THE PREFERRED EMBODIMENTS

Figure 1:
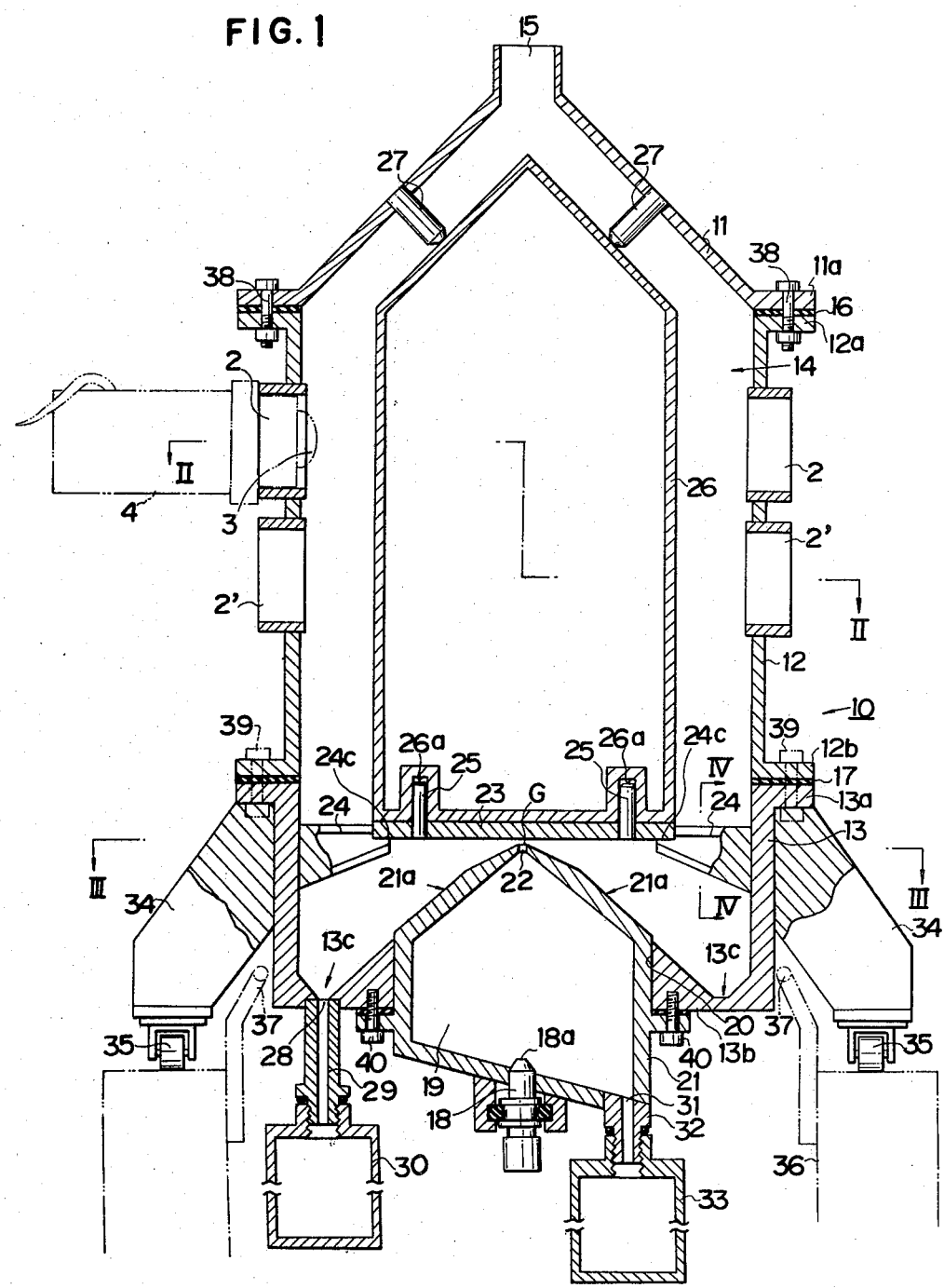
FIG. 1 is an axial cross-sectional view showing one embodiment of the inhalation toxicity testing apparatus according to the invention.

Referring to FIG. 1, an inhalation toxicity testing apparatus according to the present invention is shown as comprising an outer housing 10 which consists of a top conical cover or top segment 11, a vertically standing hollow cylindrical shell or intermediate segment 12, and a cylindrical cup-shaped base or lower segment 13. These segments are connected in this order to define a substantially cylindrical chamber 14 through which the mist of a test liquid passes. More particularly, the cover 11 is provided at its apex with an exhaust port 15 for exhausting the mist from the chamber 14 to any suitable collector through a conduit (not shown). The cover 11 includes an annular flange 11a radially and circumferentially extending from the lower end of the cover. The shell 12 includes an annular flange 12a radially and circumferentially extending from the upper end of the shell. The cover flange 11a is removably secured to the shell flange 12a via a gasket 16 by a bolt connection 38. Similarly, the shell 12 is removably connected to the base 13 by securing a lower annular flange 12b of the shell to an upper annular flange 13a of the base via a gasket 17 by a bolt connection 39.

The housing 10, more particularly, the shell 12 is provided with a plurality of openings 2 and 2'. In this embodiment, the opening 2 is defined by a ring member perpendicularly welded to the shell 12. A holder 4 for holding a small test animal 3 such as a rat in place may be in close fit with the ring member such that the nose or head of the animal is exposed to the mist in the chamber. In this embodiment, two sets of circumferentially spaced-apart openings 2 and 2' are arranged in a vertically spaced-apart relationship. For the sake of simplicity of drawing, the openings 2 of the upper set are depicted in FIG. 1 as being in alignment with the openings 2' of the lower set. However, it should be noted that the openings 2 of the upper set may preferably be circumferentially offset from the openings 2' of the lower set as shown in FIG. 2.

Figure 3:
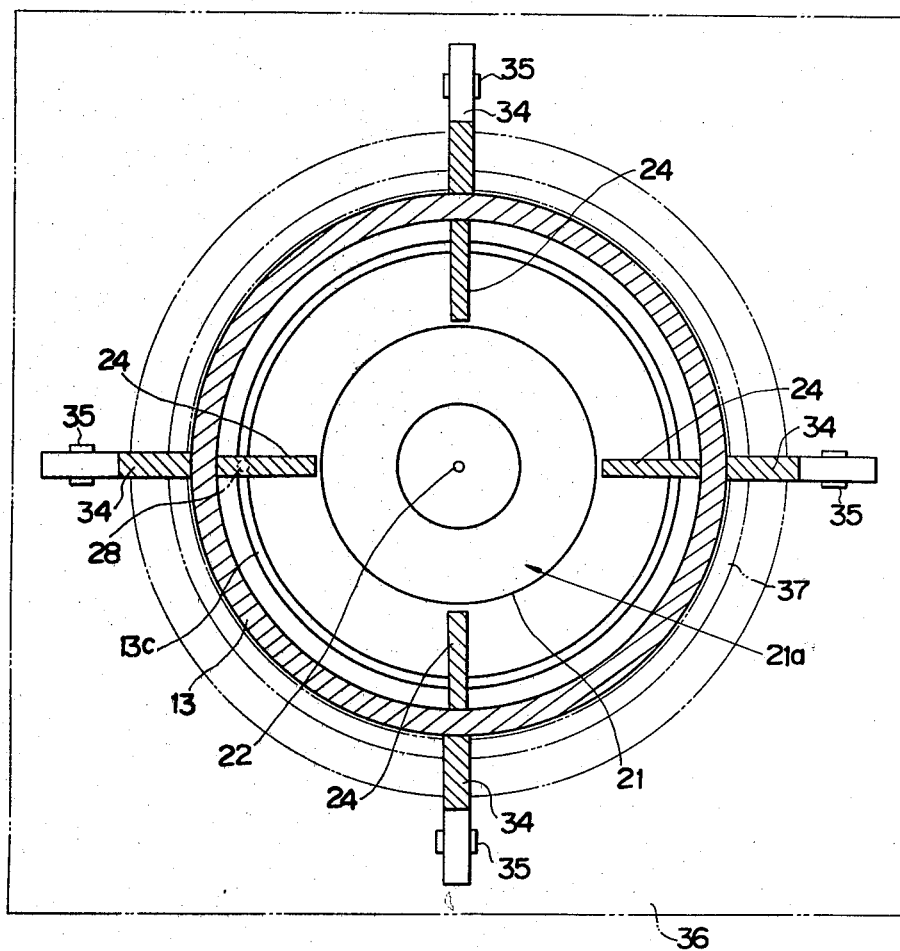
FIG. 3 is a transverse cross-sectional view of the apparatus taken along line III—III in FIG. 1.

The apparatus further includes means for supplying the mist of a test liquid into the chamber 14. The mist supplying means includes a spray nozzle 18 for spraying the test liquid in the form of mist, and a mist supply casing 21 disposed at the bottom of the housing 10 or the base 13. More specifically, the base 13 is provided at the bottom with a central opening 20. The casing 21 has a conical top wall 21a, a cylindrical side wall and an inclined bottom plate and defines a mist reservoir 19 therein. The casing 21 is removably secured to the base 13 by bolts 40 by placing the casing 21 in close fit with the central opening 20 of the base 13 so that the casing 21 is aligned with the vertical axis of the housing 10. The spray nozzle 18 is attached to the bottom plate of the casing 21 at the center with a nozzle port 18a directed vertically upward into the reservoir 19. The mist supply casing 21 also includes an injection port 22 at the apex of the conical top wall 21a. The injection port 22 vertically extends and is in alignment with the axis of the housing 10 as shown in FIG. 3. The mist reservoir 19 communicates with the chamber 14 through this injection port 22.

In the chamber 14 defined by the housing 10, a round baffle 23 is horizontally located immediately above the injection port 22. The baffle 23 is spaced a gap G from the upper end of the injection port 22 and has a substantially smaller diameter than the housing 10. A plurality of support arms 24 extend radially inward from the inner wall of the base 13 at circumferentially spaced-apart positions, in this embodiment, four equally spaced-apart positions as best shown in FIG. 3. The support arms are provided at the inward end with stepped portions 24c in which the baffle 23 is removably fitted. Accordingly, a free space is left between the outer periphery of the baffle 23 and the inner wall of the housing 10.

Figure 2:
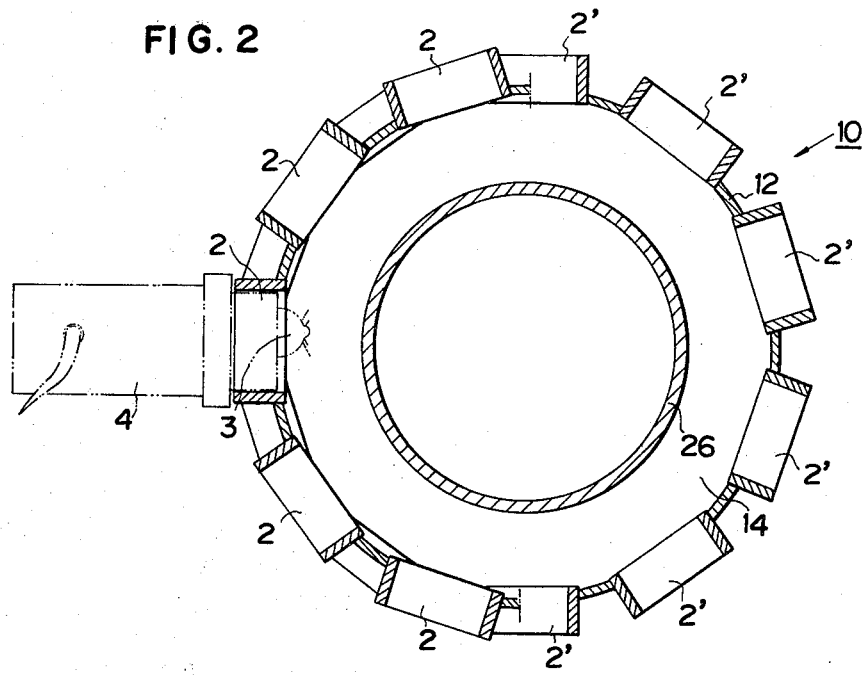
FIG. 2 is a transverse cross-sectional view of the apparatus taken along line II—II in FIG. 1.

Placed on the baffle 23 is a hollow inner housing 26 having a substantially conformable configuration to the inner configuration of the outer housing 10 as shown in FIGS. 1 and 2. A plurality of positioning studs 25 are embedded in the baffle 23 and extend vertically upward into a corresponding plurality of recesses 26a at the bottom of the inner housing 26 to retain the inner housing 26 in place. The inner housing 26 occupies a central portion of the chamber 14 above the baffle 23 is leave between the inner and outer housings a flow path extending from the level of the baffle 23 to the exhaust port 15. It is to be noted that a plurality of pins 27 embedded in the cover 11 extend inward at an angle and abut the conical top portion of the inner housing 26 to retain the inner housing upright.

Figure 4:
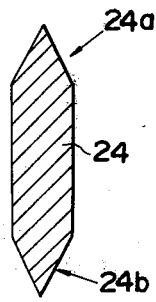
FIG. 4 is an enlarged cross-sectional view of a support arm taken along line IV—IV in FIG. 1.
Figure 5:
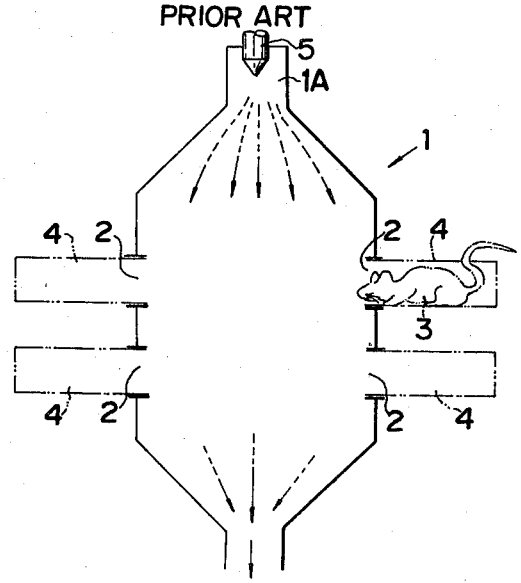
FIG. 5 is a schematic view of a prior art apparatus for use in inhalation toxicity tests according to the head exposure method.

As shown in FIG. 4, the support arm 24 has a cross section having upper and lower edges 24a and 24b which are formed by bevelling the four corners of a rectangular member.

The base 13 has a frustoconical portion concentric with central opening 20. The frustoconical surface forms a circumferentially extending channel 13c with the bottom 13b of the base for collecting condensed test liquid. The channel 13c is slightly inclined and has at the lowest position a drain port 28. A sump 30 is removably attached to the drain port 28 through a hollow pipe 29. The condensed liquid flows along the channel 13c and collects in the sump 30 through the pipe 29. On the other hand, the mist supply casing 21 is also provided at the bottom with a drain port 31 for recovering condensed test liquid. Preferably, the drain port 31 is located at the lowest position of the inclined bottom plate of the casing 21 as shown in FIG. 1. Another sump 33 is removably attached to the drain port 31 through a hollow pipe 32. The condensed liquid flows along the inclined bottom plate and collects in the other sump 33 through the pipe 32.

The base 13 has a plurality of support legs 34 rigidly secured to the base 13 and extending radially outward and vertically downward. The support leg 34 is provided at the lower end with a caster 35 which is placed on a station 36. The station 36 includes an annular guide member 37 which surrounds the lower outer surface of the base 13. Thus the whole housing 10 may be rotated about its axis.

With the above arrangement, the mist of a test liquid is passed through the chamber 14 by pumping compressed air and the test liquid to the spray nozzle 18. The nozzle 18 sprays the liquid in the form of mist vertically upward into the mist reservoir 19 through the nozzle port 18a. The mist reservoir 19 is fully filled with the mist under pressure. The upward flowing mist is converged by the conical top wall 21a toward the injection port 22, and injected upward through the injection port 22 at an accelerated velocity to impinge against the baffle 23. Inertial impingement of the mist jet against the baffle 23 serves for mist classification. The mist injected from the injection port 22 consists of test liquid droplets widely varying in size. Relatively large size droplets in the mist are adhered to and coalesced on the baffle 23 upon inertial impingement. Coalescence of droplets results in the formation of a liquid film on the baffle, from which drops drip down under gravity. The condensed liquid flows along the surfaces of the upper conical wall 21a of the casing 21 and the frustoconical portion of the base 13 into the channel 13c at the bottom of the base 13, and then collects in the sump 30 through the drain port 28.

Relatively small size droplets in the mist escape from the underside of the baffle 23 to the free space outside the baffle 23 without impinging against the baffle 23, then flow upward into the inhalation chamber 14 between the outer and inner housings 10 and 26, and reach the openings 2 and 2' where the test animals 3 inhale the mist. A major portion of the mist which is not inhaled by the animals continues to flow upward and exhausts through the exhaust port 15 with the aid of any suitable venting means.

Although the mist flowing through the inhalation chamber consists of relatively small size droplets as a result of classification due to inertial impingement of the mist jet against the baffle, some droplets can coalesce into relatively large size droplets due to relative impingement in the course of upward flow to the level of the openings 2, 2'. Also, some relatively large droplets can be entrained in the mist stream due to re-scattering at the baffle 23. However, the distance that the mist must travel upward from the baffle 23 to the openings 2, 2' causes such coalesced or entrained relatively large size droplets to settle down. As a result, the mist stream which can reach the openings 2, 2' consists essentially of droplets having a size less than a given value. In the illustrated apparatus, the classification by inertial impingement in cooperation with the settling during upward travel of the mist effectively prevents relatively large size droplets from reaching the test animals. In addition, the maximum size of droplets in the mist stream to which the animals are exposed may be limited to any desired value by a suitable choice of the diameter of the injection port 22 and/or the flow rate of mist injected through the injection port 22.

The inner housing 26 with a substantial volume defines the annular inhalation chamber 14 with the outer housing 10 so that the test liquid mist flows into a limited space adjacent the openings 2, 2' or the heads of the test animals 3. The presence of the inner housing 26 reduces the total volume of mist passing through the chamber or reduces the amount of the mist which is exhausted in vain without being inhaled by the animals, and hence, saves the amount of the test liquid consumed, as compared with prior inhalation chambers which are unoccupied by an inner housing. In the absence of the inner housing, the concentration of mist can be somewhat non-uniform in the horizontal cross section of the housing 10, introducing errors in the test results. The presence of the inner housing 26 also serves to provide a uniform concentration of mist in the cross section of the housing 10, minimizing the occurrence of errors. It is to be noted that a temperature monitoring device such as a thermistor may be set within the inner housing 26. An advantage is that such devices, which might be otherwise readily damaged, are not exposed to the mist.

In the illustrated embodiment, part of droplets in the mist generated in the reservoir 19 impinge against the inner surface of the casing 21. The impinging droplets adhere to and coalesce on the surface to form drops, which then flow down along the surface and collect in the sump 33 through the drain port 31. The liquid film on the baffle 23 resulting from adherence and coalescence of mist droplets after their impingement against the baffle 23 forms drops, which drip onto the conical surfaces of the casing 21 and the base 13, flow into the channel 13c, and then collect in the sump 30 through the drain port 28. The thus collected liquid may generally be re-used as the test liquid to be atomized by the spray nozzle 18. Preferably, a peristaltic pump (not shown) is located in a line connecting the sumps 30, 33 and the spray nozzle 18 to provide fluid communication therebetween. Then the test liquid portions collected in the sumps 30, 33 may be circulated for re-use.

As shown in FIG. 4, the support arms 24 for supporting the baffle 23 have the upper and lower sharpened edges 24a and 24b. If the support arm 24 had a rectangular cross section, the mist would impinge against the lower side of the support arm to adhere thereto and coalesce thereon when the mist flows upward from the underside past the outside of the baffle 23. Further, relatively large size droplets would accumulate on the upper side of the support arm 24 when they settle down from above the support arm. These undesired problems may be substantially eliminated by bevelling the four corners of a rectangular section into sharpened edges.

In the illustrated embodiment, the housing assembly can be rotated about its axis as it stands on the legs 34 with casters 35. With test animals 3 in the holders 4, the operator can easily attach or detach the holders 4 to or from the rings members of the outer housing 10 while progressively rotating the housing assembly. Therefore, the apparatus of the present invention requires the minimum area for its installation so that it can be placed adjacent the wall or corner of the laboratory room.

In the illustrated embodiment, the outer housing 10 consists of the conical cover or top segment 11, the cylindrical shell or intermediate segment 12, and the cup-shaped base or lower segment 13. These segments are interconnected by means of their flanges 11a, 12a, 12b, 13a and bolt connections 38, 39. The housing 10 can be readily assembled or disassembled. The inner housing 26 is readily removable as it is only placed on the baffle 23 with the positioning studs 25 received in the recesses 26a. The baffle 23 is also readily removable as it is only in engagement with the stepped portions 24c of the support arms 24. Further, the mist supply casing 21 is readily removable from the base 13 by loosening the bolts 40 and withdrawing the casing from the opening 13b. When it is scheduled that another test using a different test liquid follows, the components can be disassembled and cleaned without trouble.

In the illustrated embodiment, the test liquid mist generating means is illustrated in the form of the spray nozzle 18. The mist generating means is not limited to the spray nozzle; other conventional devices such as, for example, a ultrasonic mist generator, nebulizer and spinning-disc mist generator may be used instead. Further, the spray nozzle 18 is located at the bottom of the mist supply casing 21 in the illustrated embodiment. However, the location of the mist generating means is not limited. The mist generating means may be set separate from the casing 21 and the mist generated thereby may be directed to the reservoir 19 through a conduit.

The inhalation toxicity testing apparatus according to the present invention is basically of the construction wherein an outer housing defining an inhalation chamber therein is provided at the bottom with mist supplying means and at the top with an exhaust port such that the mist of a test liquid may flow upward the chamber. The mist to which test animals are exposed consists essentially of droplets having smaller sizes that a given value because relatively large size droplets in the mist will settle down during the upward flow of the mist independent of whether they are initially contained or newly formed as a result of coalescence of fine droplets. Accordingly, the mist free of unexpectedly large size droplets reaches the level of the test animals. If the mist that the test animals inhale contains relatively large size droplets or consists of droplets widely varying in size, the test liquid will be deposited on the organs (nasal cavity, oral cavity, air-passages or lung) of the respirator of a test animal in varying amounts, rendering toxicity evaluation inaccurate. Provision of the mist of droplets having a controlled size distribution can eliminate such errors, and as a result, the toxicity of a test agent is accurately evaluated in a consistent manner.

Particularly when a mist supply casing defining a mist reservoir and associated with mist generating means is disposed at the bottom of the outer housing, an injection port is formed at the top of the mist supply casing, and a baffle is located immediately above the injection port, the test liquid mist in the reservoir is injected through the injection port to impinge against the baffle. The inertial impingement of the mist jet against the baffle functions to classify the droplets of the mist by removing relatively large size droplets. The mist that test animals inhale thus has a controlled or uniform droplet size distribution wherein the maximum size is limited to a given value. The toxicity of a test agent is evaluated in a more accurate, consistent manner.

What is claimed is:

1. An inhalation toxicity testing apparatus of the type wherein the noses or heads of small test animals are exposed to the mist of a test liquid, comprising:

a. a vertical, hollow cylindrical outer housing defining an outer boundary of a chamber for the passage of the mist, said outer housing including a plurality of circumferentially spaced-apart openings therein, each adapted to receive the nose or head of a test animal, and an outlet at the top for exhausting the mist therethrough;

b. means, disposed in said housing below said openings, for supplying an upward flow of the test liquid in the form of mist into said chamber; said mist supplying means including mist generating means for atomizing the test liquid into mist, and means, disposed in fluid communication between said mist generating means and said chamber, for controlling the droplet size distribution of the mist by removing relatively large size droplets from the mist; said control means including:

(1) a casing disposed at the bottom of said outer housing and defining a mist reservoir for receiving the mist, said casing having a vertically extending injection port at the top thereof for injecting the mist from said reservoir into said chamber, said injection port being aligned with the vertical axis of said outer housing;

(2) a horizontal disc-shaped baffle located within said outer housing below said openings and immediately above said injection port, said baffle having a smaller diameter than said outer housing, so as to leave a free space therebetween for the passage of the mist, whereby the mist in the reservoir is injected through the injection port to impinge against said baffle for droplet size control; and (3) a plurality of circumferentially spaced-apart support arms extending radially inward from the inner wall of said outer housing below said baffle so as to support said baffle on the radially inward ends thereof; and c. an inner housing placed on said baffle and configured in substantial conformity with the inner configuration of said outer housing to define an inner boundary of said chamber, said chamber being substantially annular and being defined between said inner housing and said outer housing and extends from the free space outside said baffle to said exhaust outlet.

2. An apparatus according to claim 1 wherein the top portion of said casing is of a conical shape having said injection port formed at the apex thereof.

3. An apparatus according to claim 2 wherein the bottom of said outer housing includes a circumferentially extending channel surrounding said casing for collecting any condensed test liquid dropping from said baffle, and a first drain port penetrating the bottom of said outer housing in fluid communication with said channel.

4. An apparatus according to claim 3, wherein each of said plurality of support arms has beveled upper and lower edges.

5. An apparatus according to claim 3, wherein said casing has a conical upper surface located beneath said baffle extending between said injection port and said channel, whereby condensed test liquid dropping from said baffle drips downward along said conical upper surface into said channel.

6. An apparatus according to claim 5, wherein said outer housing includes a cover having a conical inner surface, removably mounted at the top of said outer housing and having a central vertical port for exhausting said mist from said chamber, said inner casing having a top end having a conical outer surface uniformly spaced from said conical inner surface, said cover having means for engaging said conical outer surface to maintain said inner housing upright.

7. An apparatus according to claim 5, wherein said casing includes a bottom plate having an upper surface defining the bottom of said reservoir, said upper surface being inclined to the horizontal and having a bottom end, said casing having a casing drain port at said bottom end.

* * * * *